US009448171B2

(12) United States Patent
Lazzouni et al.

(10) Patent No.: US 9,448,171 B2
(45) Date of Patent: *Sep. 20, 2016

(54) SECURITY ASPECTS OF MULTIEXPONENTIAL DECAYS

(71) Applicant: Authentix, Inc., Addison, TX (US)

(72) Inventors: Mohamed Lazzouni, Plano, TX (US); Paul A. Carr, Cupertino, CA (US); Olusola O. Soyemi, Plano, TX (US); Jeffrey L. Conroy, Allen, TX (US)

(73) Assignee: Authenix, Inc., Addison, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/728,684

(22) Filed: Jun. 2, 2015

(65) Prior Publication Data

US 2015/0260653 A1    Sep. 17, 2015

Related U.S. Application Data

(63) Continuation-in-part of application No. 13/534,798, filed on Jun. 27, 2012, now Pat. No. 9,046,486.

(51) Int. Cl.
*G01N 21/64* (2006.01)
*G07D 7/12* (2016.01)
*G07D 7/00* (2016.01)

(52) U.S. Cl.
CPC ...... *G01N 21/6408* (2013.01); *G01N 21/6458* (2013.01); *G07D 7/0066* (2013.01); *G07D 7/124* (2013.01); *G01N 21/6428* (2013.01); *G01N 2021/6439* (2013.01); *G01N 2201/0221* (2013.01)

(58) Field of Classification Search
CPC ............... G07D 7/0066; G07D 7/124; G01N 21/6408; G01N 2201/0221
See application file for complete search history.

(56) References Cited

U.S. PATENT DOCUMENTS

| | | |
|---|---|---|
| 2005/0178841 A1 | 8/2005 | Jones et al. |
| 2007/0095891 A1 | 5/2007 | Giering et al. |
| 2007/0295116 A1 | 12/2007 | Le Mercier et al. |
| 2008/0048106 A1 | 2/2008 | Blanchard et al. |
| 2009/0008454 A1 | 1/2009 | Jones et al. |
| 2010/0295878 A1* | 11/2010 | Mathea ............ G06K 19/07703 345/690 |
| 2012/0256409 A1 | 10/2012 | Giering et al. |

* cited by examiner

*Primary Examiner* — David Porta
*Assistant Examiner* — Mindy Vu

(57) ABSTRACT

At least two luminescent materials are intermingled within a security feature. The materials are selected from among a larger set of luminescent materials each having a different individual exponential decay characteristic (decay constant and initial amplitude response to the degree of excitation) for photo-luminescent emission from the respective material following excitation. The ratio of the decay constants for any two materials is greater than or equal to about 1.5. The selected materials are mixed in one of a plurality of predetermined ratios. The combined emissions from the intermingled materials appear, to an unsophisticated measuring device, to have a single exponential decay constant. Based on measurements for the decay of the combined emissions following excitation, estimates of the individual decay constants and associated initial emission amplitudes allow decoding of the particular combination of materials and/or their ratios to validate the security feature, authenticating the article.

20 Claims, 7 Drawing Sheets

Overlaid Mono and Biexponential Decays

**Time vs delta
Biexponential – single exponential
$\tau$ ratio = 1.5**

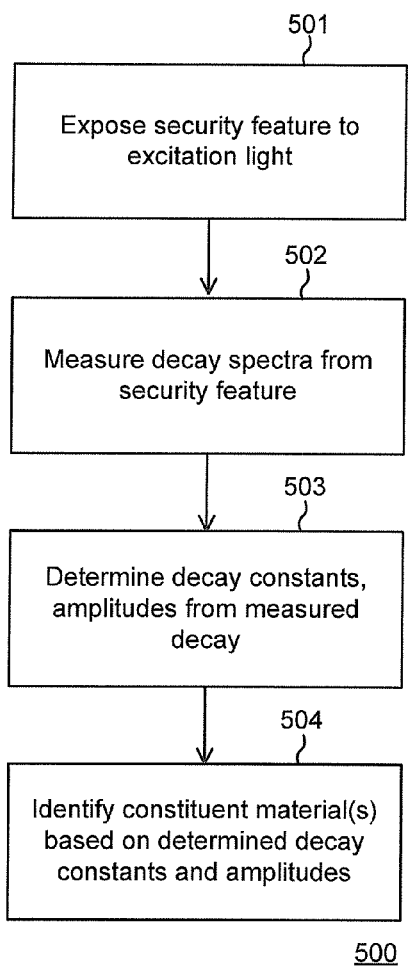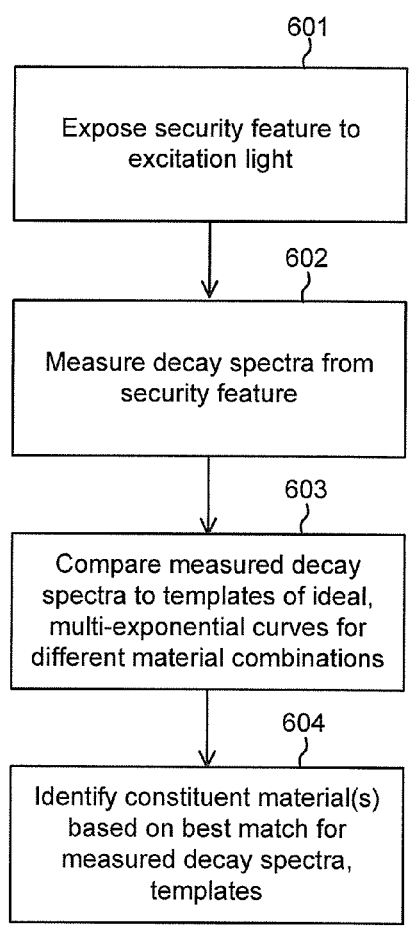

SECURITY ASPECTS OF MULTIEXPONENTIAL DECAYS

CROSS-REFERENCE TO RELATED APPLICATIONS

This application is a continuation-in-part of U.S. Non-Provisional patent application Ser. No. 13/534,798 filed Jun. 27, 2012 and entitled "SECURITY ASPECTS OF MULTI-EXPONENTIAL DECAYS," now U.S. Pat. No. 9,046,486. The content of the above-identified patent document is incorporated herein by reference.

TECHNICAL FIELD

The present disclosure relates generally to use of luminescent materials for authentication and, more specifically, to exploiting combinations of quasi-resonant luminescent materials with identical or distinct emission wavelengths.

BACKGROUND

Authentication of items such as documents, especially banknotes (currency) and the like, against forgery or counterfeiting may involve detection of the exponential decay from photoluminescence. In particular, the intensity y of time resolved emissions from quasi-resonant materials, which emit light having a similar wavelength to the excitation source, tend to be dominated by an exponential function of time (t) having the general form $$y = Ae^{-t/\tau} \quad (1)$$

where A (the amplitude) describes the intensity of the signal at time t and $\tau$ (the lifetime of the decay) provides an identifier for the specific quasi-resonant luminescent material. Security features including such materials, though proven, are growing more ubiquitous and therefore less reliable for authentication of very high security features such as those on banknotes and security documents.

SUMMARY

At least two luminescent materials are intermingled within a security feature. The materials are selected from among a larger set of luminescent materials each having a different individual exponential decay characteristic (decay constant and initial amplitude response to the degree of excitation) for photo-luminescent emission from the respective material following excitation. The ratio of the decay constants for any two materials is greater than or equal to about 1.5. The selected materials are mixed in one of a plurality of predetermined ratios. As a result of mixture, the combined emissions from the intermingled materials appear, to an unsophisticated measuring device, to have a single exponential decay constant. Based on measurements for the decay of the combined emissions following excitation, estimates of the individual decay constants and associated initial emission amplitudes allow decoding of the particular combination of materials and/or their ratios to validate the security feature, authenticating the article including the security feature.

A method of authenticating a security feature includes using an illumination source, exciting an intermingled luminescent material within the security feature, where the intermingled luminescent material comprising a plurality of luminescent materials that, when individually excited in an absence of other luminescent materials, each produce emissions with a respective individual exponential decay characteristic. The intermingled luminescent material responds to excitation with emissions at a wavelength having a single, multi-exponential decay characteristic, the single multi-exponential decay characteristic different than all of the respective individual exponential decay characteristics for the plurality of luminescent materials. A sensor is employed to measuring decay spectra from the security feature following excitation. A processing element estimates a plurality of exponential decay characteristics from the measured decay spectra that combine to form the single multi-exponential decay characteristic, and identifies materials from a selected group of materials each corresponding to one of the plurality of estimated exponential decay characteristics forming the single multi-exponential decay characteristic. The intermingled luminescent material may be affixed to a brand product. The individual exponential decay characteristics may be a respective individual decay constant for emissions following excitation for each of the plurality of luminescent materials. The plurality of luminescent materials may be selected based on a ratio of the respective individual exponential decay characteristics, where the ratio is greater than or equal to a predetermined ratio. The plurality of luminescent materials may be intermingled in the security feature to produce an overall decay of emissions from the intermingled luminescent material according to $$y = A_1 e^{-t/\tau_1} + A_2 e^{-t/\tau_2} + A_3 e^{-t/\tau_3} \ldots + A_n e^{-t/\tau_n}$$

where y is an intensity or amplitude of the emissions at time t, $A_n$ is an initial amplitude of emissions from an nth one of the plurality of luminescent materials following excitation and $\tau_n$ is a decay constant for emissions from the nth luminescent material following excitation. The emissions of the plurality luminescent materials in response to the excitation may be compared to one or more templates of multi-exponential curves to estimate a ratio of amounts of each of the plurality luminescent materials within the intermingled luminescent material. The method may include illuminating a substrate in which the intermingled luminescent material is embedded using the illumination source. One or more emission responses of the intermingled luminescent material to excitation by light having a first wavelength and to excitation by light having a second wavelength may be employed by the processing element to identify the plurality of luminescent materials.

A method of authenticating a security feature includes using an illumination source, exciting an intermingled luminescent material within the security feature, where the intermingled luminescent material comprising a plurality of luminescent materials that, when individually excited in an absence of other luminescent materials, each produce emissions with a respective individual exponential decay characteristic. The intermingled luminescent material responds to excitation with emissions at a wavelength having a single, multi-exponential decay characteristic, the single multi-exponential decay characteristic different than all of the respective individual exponential decay characteristics for the plurality of luminescent materials. A sensor is employed to measuring decay spectra from the security feature following excitation. A processing element estimates a plurality of exponential decay characteristics from the measured decay spectra that combine to form the single multi-exponential decay characteristic, and identifies materials from a selected group of materials each corresponding to one of the plurality of estimated exponential decay characteristics forming the single multi-exponential decay characteristic. The intermingled luminescent material may be affixed to a brand product. The individual exponential decay characteristics may be a respective individual decay constant for emissions following excitation for each of the plurality of luminescent materials. The plurality of luminescent materials may be selected based on a ratio of the respective individual exponential decay characteristics, where the ratio is greater than or equal to a predetermined ratio. The plurality of luminescent materials may be intermingled in the security feature to produce an overall decay of emissions from the intermingled luminescent material according to $$y = A_1 e^{-t/\tau_1} + A_2 e^{-t/\tau_2} + A_3 e^{-t/\tau_3} \ldots + A_n e^{-t/\tau_n}$$

where y is an intensity or amplitude of the emissions at time t, $A_n$ is an initial amplitude of emissions from an nth one of the plurality of luminescent materials following excitation and $\tau_n$ is a decay constant for emissions from the nth luminescent material following excitation. The emissions of the plurality of luminescent materials in response to the excitation may be compared to one or more templates of multi-exponential curves to estimate a ratio of amounts of each of the plurality luminescent materials within the intermingled luminescent material. The method may include illuminating a substrate in which the intermingled luminescent material is embedded using the illumination source. One or more emission responses of the intermingled luminescent material to excitation by light having a first wavelength and to excitation by light having a second wavelength may be employed by the processing element to identify the plurality of luminescent materials.

An automated authentication device includes an excitation source configured to illuminate the security feature for an article with light of at least one selected wavelength as the security feature is moved in front of the authentication device, where the security feature including an intermingled luminescent material comprising a plurality of luminescent materials that, when individually excited in an absence of other luminescent materials, each produce emissions with a respective individual exponential decay characteristic, wherein the intermingled luminescent material is selected to respond to illumination with the light with emissions having a single, multi-exponential decay characteristic, and where the single multi-exponential decay characteristic different than all of the respective individual exponential decay characteristics for the plurality of luminescent materials. The automated authentication device also includes at least one sensor configured to receive emissions from the security feature for the article as the security feature is moved in front of the authentication device and measure decay spectra of emissions from the security feature. The automated authentication device further includes a processing element configured to estimate a plurality of exponential decay characteristics from the measured decay spectra that combine to form the single multi-exponential decay characteristic. The article may be a brand product. The plurality of luminescent materials may be intermingled in the security feature to produce an overall decay of emissions from the intermingled luminescent material according to $$y = A_1 e^{-t/\tau_1} + A_2 e^{-t/\tau_2} + A_3 e^{-t/\tau_3} \ldots + A_n e^{-t/\tau_n}$$

where y is an intensity or amplitude of the emissions at time t, $A_n$ is an initial amplitude of emissions from an nth one of the plurality of luminescent materials following excitation and $\tau_n$ is a decay constant for emissions from the nth luminescent material following excitation. The security feature may be moved in front of the authentication device using one of a document feeder and an article conveyor.

BRIEF DESCRIPTION OF THE DRAWINGS

For a more complete understanding of the present disclosure and its advantages, reference is now made to the following description taken in conjunction with the accompanying drawings, in which like reference numerals represent like parts:

FIG. 5 is a high level flow diagram for detecting multi-exponential decays during document authentication according to one or more embodiments of the present disclosure;

FIG. 6 is a high level flow diagram for an alternate, template-based process of article authentication according to one or more embodiments of the present disclosure;

DETAILED DESCRIPTION

FIGS. 1 through 8, discussed below, and the various embodiments used to describe the principles of the present disclosure in this patent document are by way of illustration only and should not be construed in any way to limit the scope of the disclosure.

Figure 1:
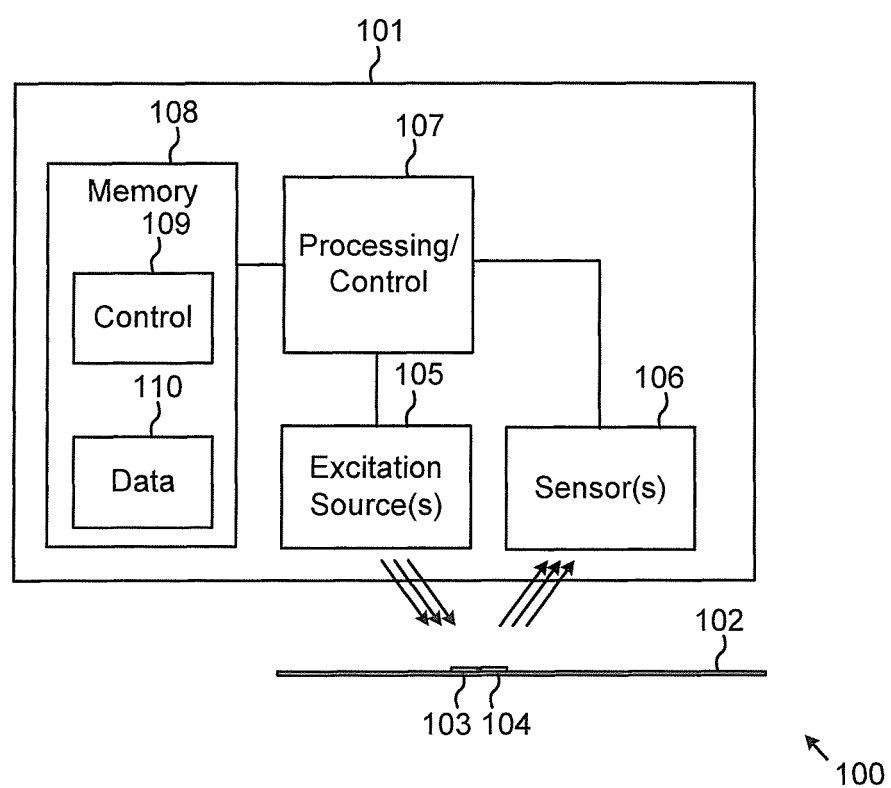
FIG. 1 is a high level block diagram illustrating an authentication system for exploiting security features of multi-exponential decays during document authentication according to one or more embodiments of the present disclosure.

FIG. 1 is a high level block diagram illustrating an authentication system for exploiting security features of multi-exponential decays during document authentication according to one or more embodiments of the present disclosure. The authentication system 100 includes an authentication device 101, which is preferably configured to be operated by a user as a handheld device (that is, with the components disposed within a body suitable to be handheld and manually operated). The authentication device is employed by the user to authenticate a document 102 on which are affixed, or in which are embedded, a plurality of quasi-resonant luminescent materials 103, 104 within or forming part of a security device for the document 102, as described in further detail below.

Authentication device 101 includes a source 105 of infrared excitation light, which may alternatively be visible or ultraviolet. Preferably the dominant portion of light emitted by source 105 is at or near wavelengths with which luminescent materials 103, 104 are resonant, and which will prompt emission of light by luminescent materials 103, 104.

Optical filters may be employed in front of source 105 to increase the selectivity of wavelengths for light impinging on document 102 and the security features including luminescent materials 103, 104. Source 105 may actually be formed of multiple individual but coordinately operated light sources, such as for example a row of light emitting diodes (LEDs).

Authentication device 101 also includes one or more sensors 106 for detecting light emitted by luminescent materials 103, 104. Preferably sensors 106 are most responsive to light at or near wavelengths emitted by luminescent materials 103, 104 in response to excitation light from source 105. Optical filters positioned in front of sensors 106 may improve the selectivity of wavelengths impinging on sensors 106, improving signal-to-noise ratios, and various known signal conditioning and signal processing techniques may likewise be employed to filter the target wavelengths. A plurality of optical sensing devices such as photodiodes may be employed as sensor 106, with the outputs of those sensing devices either summed or averaged for use in authentication.

An integrated circuit processing and control element 107, such as a programmable microprocessor or microcontroller, is coupled to both excitation source 105 and sensors 106, and controls operation of both. That is, processing/control element 107 controls actuation of excitation sources 105 and sampling of the output(s) of sensors 106. The processing/control element 107 is coupled to a memory 108, which may hold both a control program 109 stored in a preferably nonvolatile but reprogrammable portion of memory 108 and a data store 110. Although depicted as separate components in FIG. 1, all or some portion of memory 108 may be formed within same packaged integrated circuit as processing/control element 107. Moreover, while depicted as mounted within authentication device 101 in the exemplary embodiment of FIG. 1, processing/control element 107 and/or memory 108 may actually be part of a separate data processing system, with handheld authentication device 101 functioning as a peripheral device to that data processing system can processing/control element 107 coupled by connectors or wireless data communication to excitation source 105 and sensors 106. In addition, to the extent that processing/control element 107 and memory 108 are internal to handheld authentication device 101, a wired or wireless communication port (not shown) may allow handheld authentication device 101 to transmit data to an external data processing system (also not shown in FIG. 1), so that a portion of the processing described below may be performed in that system.

In alternative implementations, authentication device 101 may not necessarily be a handheld device. The authentication device 101 may form part of a sensor (e.g., for automation), where the sensor remains stationary and a marker including the luminescent materials as described below is moved in front of the sensor(s) 106. Movement of the article to be authenticated may be by a feeding or conveying mechanism. The rate of movement should be sufficiently slow to allow an excitation source(s) 105 to illuminate a security feature on the article to be authenticated, and to allow the sensor(s) 106 to measure decay spectra resulting from that illumination. The authentication device 101 may therefore allow, for example, authentication of a part having the marker embedded therein during automated assembly or fabrication of an article such as a circuit board on which integrated circuits are mounted, a mechanical system such as a high performance engine, or a luxury article of apparel or furniture. In other alternatives, the marker may be on a badge employed for access control, with the badge moved in front of a security scanner including the sensor for authentication. In still other alternatives, the sensor may be integrated into a bill validator, with a document (bill) feeder moving the security feature in front of the sensor(s) 106. In that manner or in a similar fashion, the sensor(s) 106 be employed to authenticate payment in a unattended retail environment. In other embodiments, the sensor(s) 106 may be employed in an airport security scanner, with an article conveyor moving the security feature in front of the sensor (s) 106. In other embodiments, the sensor(s) 106 may be employed to validate seals on packaging formed so that opening the package destroys the marker or security feature, rendering the security feature incapable of being authenticated.

Those skilled in the art will recognize that the complete structure and operation of an authentication system is not depicted in the drawings or described above. Instead, for simplicity and clarity, only so much of an authentication system as is unique to the present disclosure or necessary for an understanding of the present disclosure is depicted and described herein. In addition, while the exemplary embodiment relates to authentication of security features on documents, the principles of the present disclosure may be readily applied to security features in a wide variety of articles, including liquids as well as solid articles.

Luminescent materials 103, 104 in the exemplary embodiment are preferably affixed to document 102 in the form of one or more inks applied to the document 102. Alternatively, however, the security feature may be included in one or more of a fiber, substrate, opacifying layer, label, hologram, or thread forming part of document 102. In some embodiments, the document including the security feature may be affixed to brand products, such as: labels or tags on purses, shoes, or articles of apparel; and holograms or similar stickers on sunglasses, mobile phones, tablets, computers, the packaging for any such device, and/or on accessories (or the packaging for the accessories) for any such device. In some embodiments, the security feature may not be affixed to a document, but may instead be affixed or applied directly to the article to be authenticated—that is, the brand product that may be counterfeited.

Although diagrammatically depicted in FIG. 1 as affixed to separate portions of document 102, in practice the two materials may be intermingled across a single region of the surface area of document 102. To the extent excited by different wavelengths or different ranges or wavelengths of light, luminescent materials 103, 104 are preferably excited by (or resonate to) wavelengths at or near each other or to overlapping ranges of wavelengths, with excitation source 105 emitting light predominantly at those wavelengths. Similarly, to the extent that luminescent materials 103, 104 emit light at different wavelengths when excited by a common source or concomitant sources, for purposes of exciting a specific luminescent material in order to compare the emission decay spectra response to an expected response for an authentic security feature, the wavelength(s) of the emitted light are preferably at or near each other or within overlapping ranges of wavelengths, at amplitudes measurably detectable by sensors 106.

Luminescent materials 103, 104 are photoluminescent (fluorescent and/or phosphorescent), emitting light as a result of absorption of photons within light from the excitation source 105. Luminescent materials 103, 104 exhibit different decay characteristics for light emitted in response to light from the excitation source 105. Thus, rather than an intensity y of emitted light conforming to equation (1)

above, the combined light emitted from luminescent materials 103, 104 is a bi-exponential decay of the form $$y = A_1 e^{-t/\tau_1} + A_2 e^{-t/\tau_2}, \quad (2)$$

where y is an intensity or amplitude at time t and $A_1$ and $A_2$ are initial intensities or amplitudes of emitted light from materials 103 and 104, respectively. Luminescent materials 103, 104 thus offer an additional tier of security and authentication reliability as compared to materials exhibiting simple mono-exponential decay.

Figure 2:
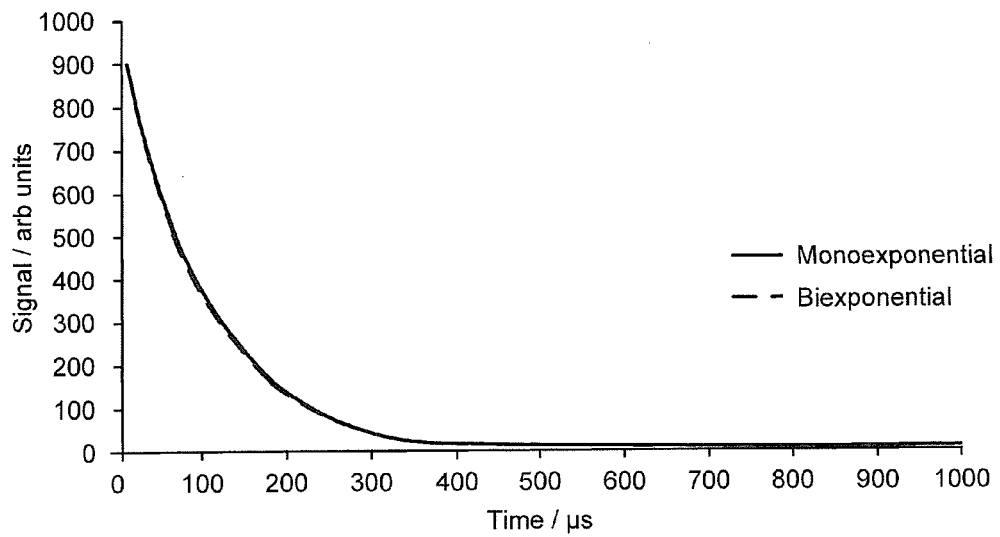
FIG. 2 is a plot comparatively illustrating a typical bi-exponential decay curve relative to a closely overlapping mono-exponential decay curve.

FIG. 2 is a plot comparatively illustrating a typical bi-exponential decay curve relative to a closely overlapping mono-exponential decay curve. The difficulty of differentiating or discriminating between mono-exponential and bi-exponential functions is well known, and is exploited in the present disclosure to provide the additional tier of security and authentication reliability described above. FIG. 2 depicts two curves for a signal measured in arbitrary units as a function of time in microseconds (µs). One of the curves depicted illustrates a mono-exponential decay function with a single decay constant τ; the other curve illustrates a bi-exponential decay function of similar overall decay but with two different decay constants, $\tau_1$ and $\tau_2$. As evident from the plot, the two curves are visually indistinguishable.

Luminescent materials 103, 104 employed for authentication in the present disclosure are characterized different decay constants $\tau_1$ and $\tau_2$ as shown in equation (2) above (e.g., material 103 is characterized by decay constant $\tau_1$ while material 104 is characterized by decay constant $\tau_2$). Depending upon the ratio of the decay constants $\tau_1$ and $\tau_2$ for a bi-exponential decay function, differences between mono-exponential and bi-exponential decay may not be visually detectable using the unaided human eye, but may be reliably distinguished in a straightforward fashion using sensitive detection equipment and sophisticated signal processing algorithms. If the ratio of the decay constants $\tau_1$ and $\tau_2$ for two different materials is equal to a minimum of about 1.5, the two lifetimes may be separated. Accordingly, the techniques of the present disclosure serve to disguise a sophisticated covert signature as a less sophisticated, still covert signature.

It should be noted that materials with decay constant ratios less than 1.5 are not precluded from functioning in the manner described above within a security feature. Rather, separation of the decay lifetimes in the presence of typical signal-to-noise ratios is simply more consistent and reliable using known signal processing techniques when the ratio is about 1.5 or greater.

Referring once again to FIG. 2, the mono-exponential curve illustrated therein represents decay with an initial amplitude A of 1000 (arbitrary units) and a decay constant τ of about 100 µs. The bi-exponential curve within FIG. 2 represents the aggregate of a first signal having an initial amplitude $A_1$ of 500 and a decay constant $\tau_1$ of about 80 us together with a second signal having an initial amplitude $A_2$ of 500 and a decay constant $\tau_2$ of about 120 µs. The ratio of decay constants for the bi-exponential curve is thus about 1.5. The similarity of the bi-exponential function in FIG. 2 to the overlaid mono-exponential function is evident, and the difference between the two functions is unlikely to be detected by a typical handheld security phosphorescence detection system. Notably, while the magnitude of amplitudes $A_1$ and $A_2$ in the example of FIG. 2 are appreciable, the difference over time for the bi-exponential function relative to the mono-exponential function is vanishingly small.

Figure 3:
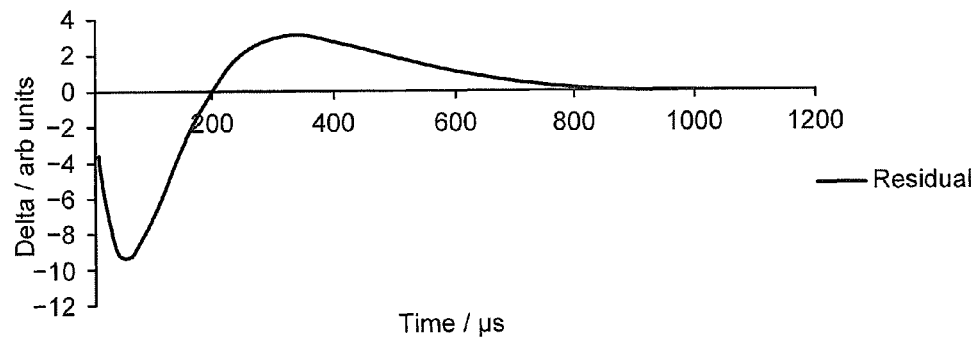
FIG. 3 is a plot illustrating the result of subtracting the mono-exponential function plotted in FIG. 2 from the overlaid bi-exponential function.

FIG. 3 is a plot illustrating the result of subtracting the mono-exponential function plotted in FIG. 2 from the overlaid bi-exponential function. The residual difference ("delta") as a function of time for the difference between the two overlaid functions demonstrates that a difference between the two functions exists, but diminishes as the functions progress toward substantially complete decay. Notably, the magnitude of the delta is very small relative to the dynamic range of the two functions plotted in FIG. 2, spanning about 12 units out of at least 900 units. As a result, sufficient signal-to-noise characteristics must be ensured for differentiation of a bi-exponential decay from a mono-exponential decay.

The bi-exponential decay security feature described in the present disclosure may be realized in at least two ways. First, a single material with implicit bi-exponential decay may be manufactured and employed. Alternatively (and preferably), however, mixtures of mono-exponential materials may be made at different ratios, yielding a system with inherent bi-exponential decay security and also offering a number of unique "codes." Thus, for example, if eight different materials each having measurably different decay constants $\tau_1$, $\tau_2$, $\tau_3$, $\tau_4$, $\tau_5$, $\tau_6$, $\tau_7$ and $\tau_8$ are available for pairing in any permutation having an acceptable ratio of decay constants, a large number of distinguishable bi-exponential decay security features may be implemented. The exact number of possible "codes" depends on the tolerance to which the mono-exponential decay constant materials may be manufactured, together with the amplitude resolution of the authentication device 101.

The concepts described above also extend readily to multi-exponential decay constants produced by combinations of three, four, or n different materials:

$$y = A_1 e^{-t/\tau_1} + A_2 e^{-t/\tau_2} + A_3 e^{-t/\tau_3} \ldots + A_n e^{-t/\tau_n}. \quad (3)$$

In a mixture of three or more materials, the ratio of the closest pairs of decay constants for materials within the combination should be greater than or equal to about 1.5 to allow reliable differentiation of the materials. That is, where three materials having three different decay constants $\tau_1$, $\tau_2$, and $\tau_3$ such that $\tau_1 < \tau_2 < \tau_3$ are employed for a security feature, the ratio of $\tau_2$ to $\tau_1$ should be about 1.5 or greater and the ratio of $\tau_3$ to $\tau_2$ should likewise be about 1.5 or greater. If a fourth material having a decay constant $\tau_4 > \tau_3$ is added, the ratio of $\tau_4$ to $\tau_3$ should be about 1.5 or greater. Thus, although exemplary embodiments described herein relate to use of only two different materials having different decay constants within a security feature, any number of materials may be utilized to form a multi-exponential decay constant, subject only to the properties of materials available. As noted above, differentiation when decay constant ratios are less than about 1.5 is possible but more difficult in the presence of typical noise.

Figure 4A:
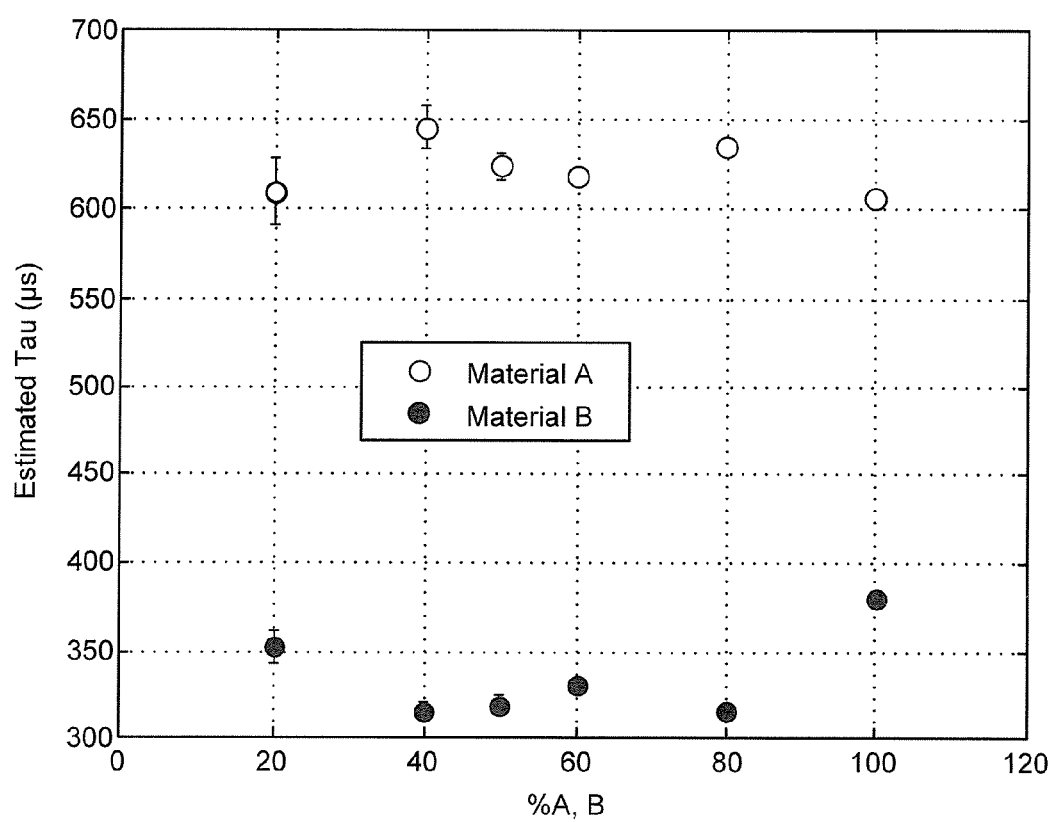
FIGS. 4A and 4B are plots of the decay constants and amplitudes, respectively, for mixtures of two separate mono-exponential decay materials in different ratios according to one embodiment of the present disclosure.
Figure 4B:
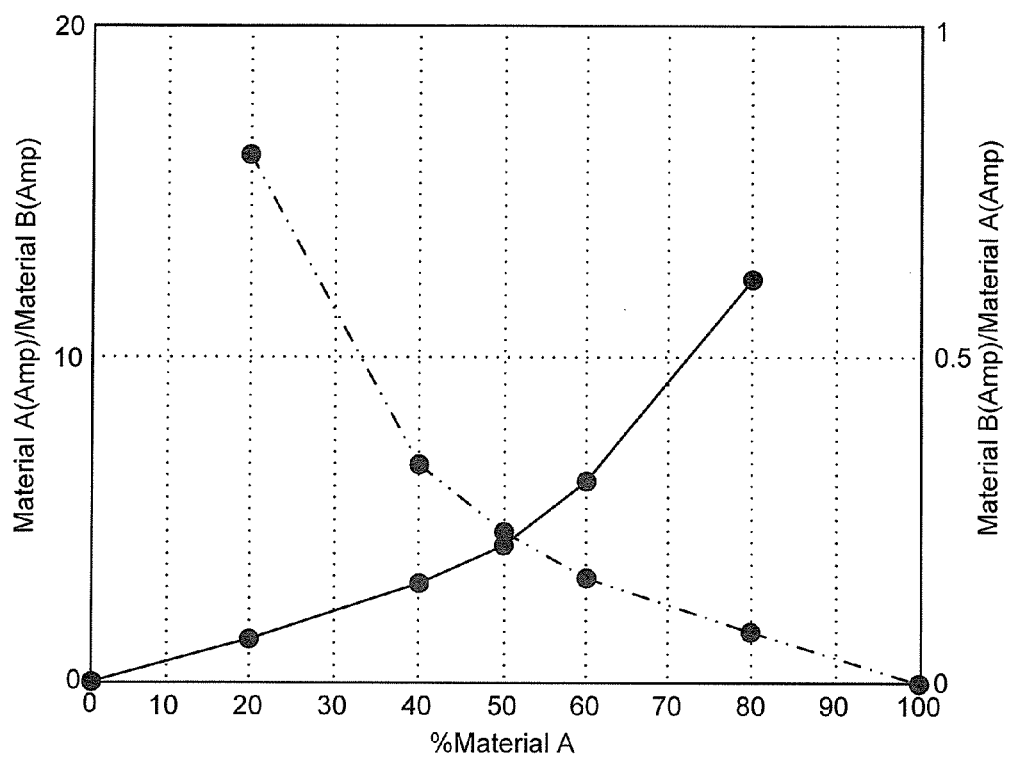

FIGS. 4A and 4B are plots of the decay constants and amplitudes, respectively, for mixtures of two separate mono-exponential decay materials in different ratios according to one embodiment of the present disclosure. A number of mixtures of two materials A and B having distinct decay constants $\tau_1$ and $\tau_2$ were formulated into an ink with the following relative concentrations: 0% A and 100% B; 20% A and 80% B; 40% A and 60% B; 50% A and 50% B; 60% A and 40% B; 80% A and 20% B and 100% A and 0% B. Decay spectra were measured with a handheld device and processed to estimate decay constants $\tau_1$ and $\tau_2$, as well as the amplitudes $A_1$ and $A_2$, for each material A and B, respectively. A test statistic detecting the presence of auto-correlation (a relationship between values separated from each other by a given time lag) in the residuals (prediction errors) from a regression analysis, was employed together with curve-fitting to confirm the nature of the exponential decay measurements (i.e., single or double), followed by estimation of the decay constants $\tau_1$ and $\tau_2$.

FIG. 4A shows the estimated decay constants $\tau_1$ and $\tau_2$ for the different ratios of mixtures of materials A and B, while FIG. 4B shows the relative amplitudes. As can be seen from FIG. 4A, the decay constants $\tau_1$ and $\tau_2$ remained consistent regardless of the material concentration. The estimate for decay constant $\tau_1$ for material A was consistently within the range of 600-650 µs, regardless of the relative amount of material A within the overall formulation, while the range of estimates for decay constant $\tau_2$ for material B was generally about 350 µs. Thus, the presence of material A and material B within the security feature may be verified based on the determination of decay constants $\tau_1$ and $\tau_2$ from the measured decay spectra following excitation. Other materials having a distinct decay constant (e.g., in the range of 100-150 τs, or in the range of 450-500 µs) could be substituted for either of material A and material B to formulate a distinct bi-exponential security feature.

FIG. 4B illustrates the estimates of the amplitudes $A_1$ and $A_2$ for materials A and B based on the measured decay spectra from each ink mixture following excitation, specifically of the ratio of those amplitudes. Plotted on overlaid vertical scales are two curves, one (solid curve) representing the ratio of the amplitude $A_1$ for material A to the amplitude $A_2$ for material B while the other (dashed curve) represents the ratio of the amplitude $A_2$ for material B to the amplitude $A_1$ for material A. As evident, the relative concentrations of materials A and B within a given formulation can be determined based on the estimated amplitude ratios. Accordingly, the combination of estimates for decay constants $\tau_1$ and $\tau_2$ and amplitudes $A_1$ and $A_2$ may be employed to distinguish not only the identity of materials A and B within a mixture used for a security feature, but also the ratio of material A to material B within that mixture.

Multiple, spaced-apart wavelengths of excitation illumination may be employed in authenticating a security feature. Multi-exponential security features may be formed of blends of different luminescent materials ("markers") that respond differently to different, spaced-apart wavelengths of excitation illumination, whether in the ultraviolet (UV) or near infrared (NIR) spectrum. For example, luminescent material A may respond in a first manner when illuminated by UV-A light having a wavelength centered around 365 nanometers (nm), in a second, different manner when illuminated by UV-B light having a wavelength centered around 313 nm, and/or in a third manner when illuminated by UV-C light having a wavelength centered around 254 nm. (The UV-A, UV-B and UV-C wavelengths are selected for purposes of explanation only). A second luminescent material, material B, may have substantially the same response to UV-A and UV-B illumination, and no response to UV-C illumination. A security feature may contain a mixture of material A and material B, and thus have a characteristic response to illumination at the wavelengths of UV-A, UV-B and UV-C. As noted above, for excitation illumination of a particular one of the spaced apart wavelengths, the wavelength(s) of the emitted light are preferably at or near each other or within overlapping ranges of wavelengths, at amplitudes measurably detectable by sensors 106, decaying to negligible levels between the spaced apart wavelengths.

FIG. 5 is a high level flow diagram for detecting multi-exponential decays during document authentication according to one or more embodiments of the present disclosure. The process 500 may be executed within a processor, such as processing and control element 107, based on one or more software modules comprising a program of executable instructions stored within a memory, such as control 109, operating in conjunction with excitation source(s) 105 and sensor(s) 106. The process 500 begins with causing an illumination of the security feature of a document to be authenticated with excitation light (step 501). Such illumination may involve pulsing the excitation source, or continuous actuation of the excitation source for at least a minimum time period. Once illumination with the excitation light is terminated, measurements of the decay spectra for the emissions from the security feature being tested are received (step 502). The measurements involve sampling with at least a predetermined frequency (e.g., every 1 to 100 µs) over a period of 100 to 2,000 µs, depending on the materials employed in the security feature being tested. Estimates of decay constants and amplitudes are then determined from the measured decay data (step 503), in the manner discussed above. Finally, the constituent materials and/or concentrations within the security feature being tested are identified based on the estimated decay constants and amplitudes (step 504). Characteristics of a selected group of materials used for security features may be used to identify the particular materials present in the security feature (or counterfeit thereof), based on the estimated decay constants. The identified combination of materials and concentrations can then be compared to expectations for the security feature, to determine a likelihood of whether the document is authentic.

FIG. 6 is a high level flow diagram for an alternate, template-based process of article authentication according to one or more embodiments of the present disclosure. The process 600 may be executed within a processor, such as processing and control element 107, based on one or more software modules comprising a program of executable instructions stored within a memory, such as control 109, operating in conjunction with excitation source(s) 105 and sensor(s) 106. The process 600 begins with causing illumination of the security feature of a document to be authenticated with excitation light (step 601), in the same manner as described above with respect to FIG. 5. Once illumination with the excitation light is terminated or paused, the decay spectra for the emissions from the security feature being tested are measured (step 602), again in the same manner as described above with respect to FIG. 5. As with the process of FIG. 5, the excitation and measurement may be repeated for collection of a set of measure decay spectra that may then be averaged and/or subject to other statistical datapoint selection or filtering. The measured decay spectra are then compared to templates for multi-exponential curves corresponding to different material combinations (step 603). The templates may be developed using a statistical classification module developing models of responses for various material combinations and identifying ideal multi-exponential response curves for each combination, and optionally tolerances or ranges for such curves. Finally, the constituent materials and/or concentrations within the security feature being tested are identified based on a best match between the measured decay spectra and the templates (step 604). Various known statistical matching or curve-fitting algorithms may be employed for determining the best match, depending upon the particular application and data characteristics.

Figure 7:
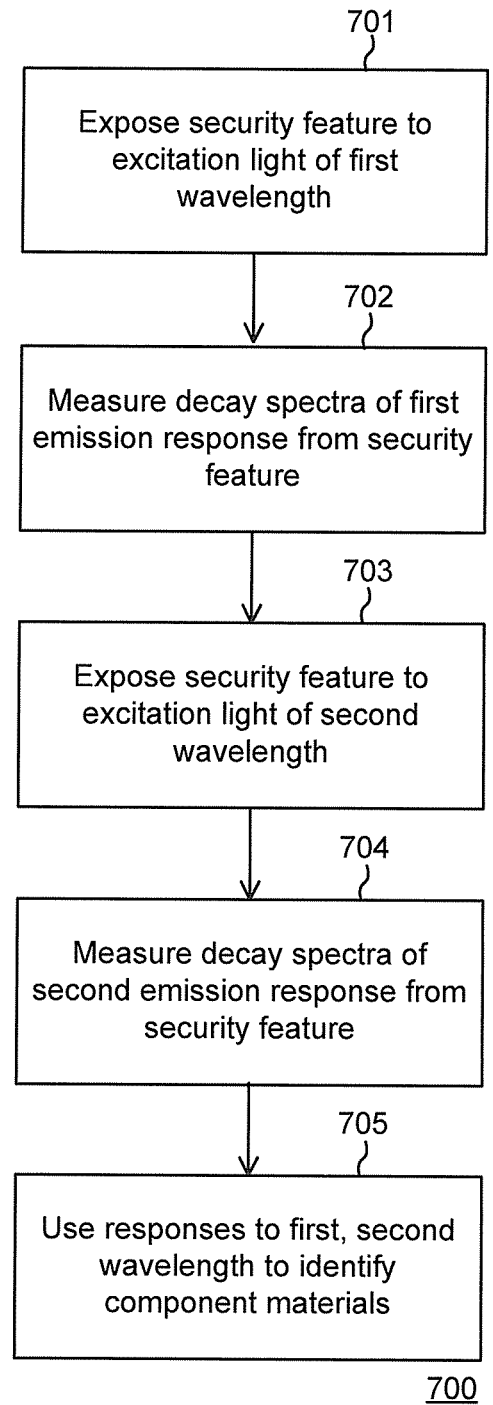
FIG. 7 is a high level flow diagram for use of excitation illumination having different wavelengths during article authentication according to one or more embodiments of the present disclosure.

FIG. 7 is a high level flow diagram for use of excitation illumination having different wavelengths during article authentication according to one or more embodiments of the present disclosure. The process 700 may be executed within a processor, such as processing and control element 107, based on one or more software modules comprising a program of executable instructions stored within a memory, such as control 109, operating in conjunction with excitation source(s) 105 and sensor(s) 106. The process 700 may also be employed in combination with either of the processes 500, 600 depicted in FIGS. 5 and 6. The process 700 begins with causing illumination of the security feature of a document to be authenticated to excitation light having a first, pre-selected wavelength (step 701), in the same manner as described above with respect to FIG. 5. The decay spectra for the emissions from the security feature being tested in response to excitation with light having the first wavelength are measured (step 702), again in the same manner as described above with respect to FIG. 5. The security feature of the article to be authenticated is then caused to be illuminated by excitation light having a second, pre-selected wavelength (step 703), in a manner consistent with the exposure to light having the first wavelength. The decay spectra for the emissions from the security feature being tested in response to excitation with light having the second wavelength are measured (step 704). The responses of the security feature to light having the first and second wavelengths are then determined to classify the component materials within the security feature (step 705). The measured decay spectra may also be concurrently employed to authenticate the proportions of component materials within the security feature. In practice, the excitation and measurement steps might be repeated to collect more response samples for improved accuracy. In addition, while depicted as separate steps, the first and second excitation steps and the first and second measurement steps could be performed concurrently or in a partially overlapping manner. For concurrent excitation, a single emission response may be sufficient to identify the constituent luminescent materials within the security feature based upon characteristics of that response.

The present disclosure describes a method of employing multi-exponential decay detection in article security and authentication. Specific decay signatures are generated by blending specific decay materials together in particular ratios, to encode a complex bi-exponential decay signature that nominally appears to be a simplistic mono-exponential decay.

Figure 8:
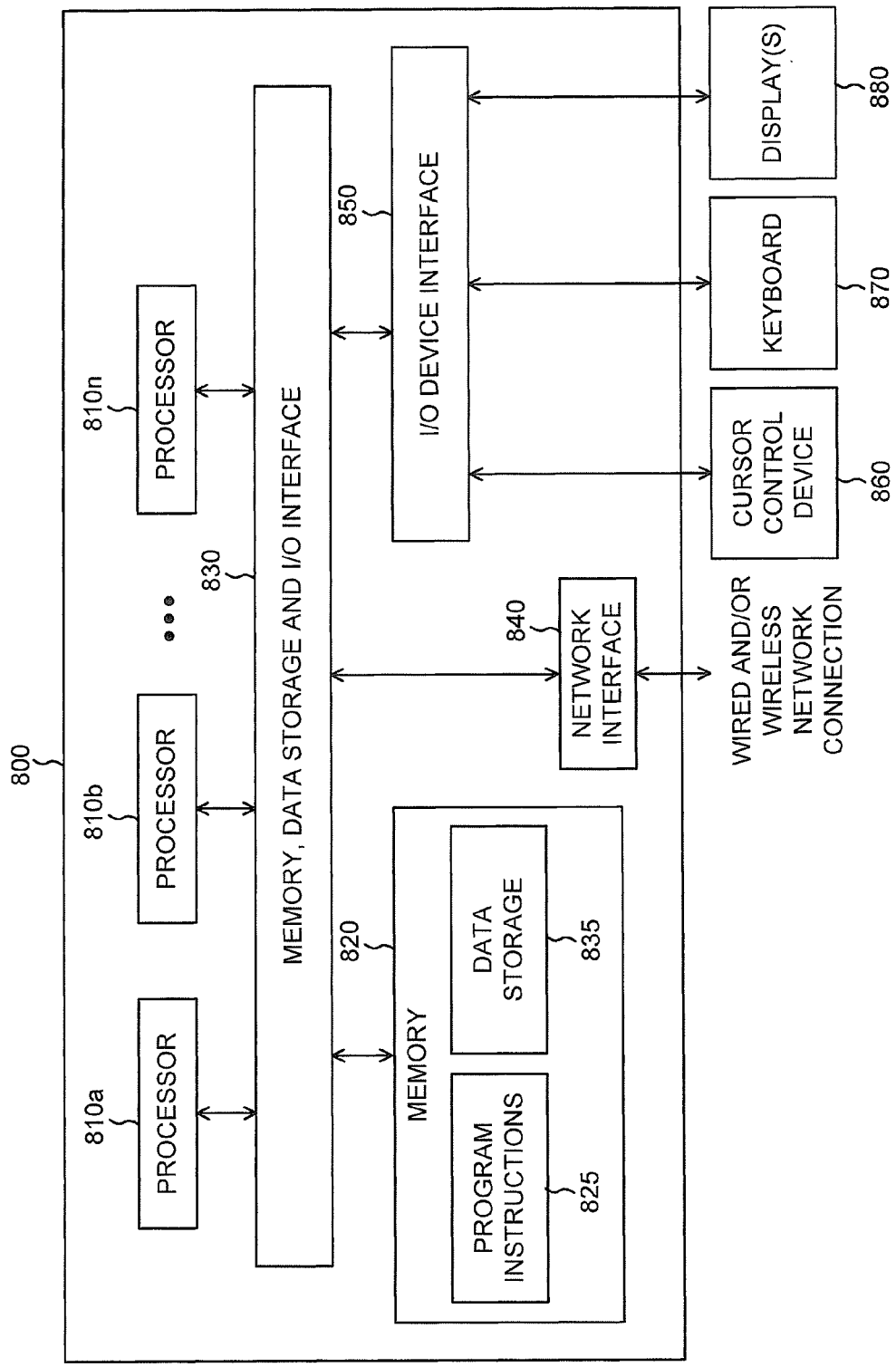
FIG. 8 is a block diagram of an exemplary data processing system that may be configured to implement the systems and methods, or portions of the systems and methods, described in the preceding figures.

Aspects of authentication device 101 and other systems depicted in the preceding figures or described above may be implemented or executed by one or more computer systems. One such computer system is illustrated in FIG. 8. In various embodiments, computer system 800 may be a server, a mainframe computer system, a workstation, a network computer, a desktop computer, a laptop, or the like. Each computer system depicted and described as a single, individual system in the simplified figures and description of this disclosure can each be implemented using one or more data processing systems, which may be but are not necessarily commonly located. For example, as known to those of skill in the art, different functions of a server system may be more efficiently performed using separate, interconnected data processing systems, each performing specific tasks but connected to communicate with each other in such a way as to together, as a whole, perform the functions described herein for the respective server system. Similarly, one or more of multiple computer or server systems depicted and described herein could be implemented as an integrated system as opposed to distinct and separate systems.

As illustrated, computer system 800 includes one or more processors 810a-810n coupled to a system memory 820 via a memory/data storage and I/O interface 830. Computer system 800 further includes a network interface 840 coupled to memory/data storage and interface 830, and in some implementations also includes an I/O device interface 850 (e.g., providing physical connections) for one or more input/output devices, such as cursor control device 860, keyboard 870, and display(s) 880. In some embodiments, a given entity (e.g., authentication device 101) may be implemented using a single instance of computer system 800, while in other embodiments the entity is implemented using multiple such systems, or multiple nodes making up computer system 800, where each computer system 800 may be configured to host different portions or instances of the multi-system embodiments. For example, in an embodiment some elements may be implemented via one or more nodes of computer system 800 that are distinct from those nodes implementing other elements (e.g., a first computer system may implement a statistical classification engine while another computer system may implement a matching module).

In various embodiments, computer system 800 may be a single-processor system including only one processor 810a, or a multi-processor system including two or more processors 810a-810n (e.g., two, four, eight, or another suitable number). Processor(s) 810a-810n may be any processor(s) capable of executing program instructions. For example, in various embodiments, processor(s) 810a-810n may each be a general-purpose or embedded processor(s) implementing any of a variety of instruction set architectures (ISAs), such as the x86, POWERPC, ARM, SPARC, or MIPS ISAs, or any other suitable ISA. In multi-processor systems, each of processor(s) 810a-810n may commonly, but not necessarily, implement the same ISA. Also, in some embodiments, at least one processor(s) 810a-810n may be a graphics processing unit (GPU) or other dedicated graphics-rendering device.

System memory 820 may be configured to store program instructions 825 and/or data (within data storage 835) accessible by processor(s) 810a-810n. In various embodiments, system memory 820 may be implemented using any suitable memory technology, such as static random access memory (SRAM), synchronous dynamic RAM (SDRAM), nonvolatile/Flash-type memory, solid state disk (SSD) memory, hard drives, optical storage, or any other type of memory, including combinations of different types of memory. As illustrated, program instructions and data implementing certain operations, such as, for example, those described herein, may be stored within system memory 820 as program instructions 825 and data storage 835, respectively. In other embodiments, program instructions and/or data may be received, sent or stored upon different types of computer-accessible media or on similar media separate from system memory 820 or computer system 800. Generally speaking, a computer-accessible medium may include any tangible, non-transitory storage media or memory media such as magnetic or optical media—e.g., disk or compact disk (CD)/digital versatile disk (DVD)/DVD-ROM coupled to computer system 800 via interface 830.

In an embodiment, interface 830 may be configured to coordinate I/O traffic between processor 810, system memory 820, and any peripheral devices in the device, including network interface 840 or other peripheral interfaces, such as input/output devices 850. In some embodiments, interface 830 may perform any necessary protocol, timing or other data transformations to convert data signals from one component (e.g., system memory 820) into a format suitable for use by another component (e.g., processor(s) 810a-810n). In some embodiments, interface 830 may include support for devices attached through various types of peripheral buses, such as a variant of the Peripheral Component Interconnect (PCI) bus standard or the Universal Serial Bus (USB) standard, for example. In some embodiments, the function of interface 830 may be split into two or more separate components, such as a north bridge and a south bridge, for example. In addition, in some embodiments some or all of the functionality of interface 830, such as an interface to system memory 820, may be incorporated directly into processor(s) 810a-810n.

Network interface 840 may be configured to allow data to be exchanged between computer system 800 and other devices attached to a common network, such as other computer systems, or between nodes of computer system 800. In various embodiments, network interface 840 may support communication via wired or wireless general data networks, such as any suitable type of Ethernet network, for example; via telecommunications/telephony networks such as analog voice networks or digital fiber communications networks; via storage area networks such as Fiber Channel storage area networks (SANs); or via any other suitable type of network and/or protocol.

Input/output devices 850 may, in some embodiments, include one or more display terminals, keyboards, keypads, touch screens, scanning devices, voice or optical recognition devices, or any other devices suitable for entering or retrieving data by one or more computer system 800. Multiple input/output devices 860, 870, 880 may be present in computer system 800 or may be distributed on various nodes of computer system 800. In some embodiments, similar input/output devices may be separate from computer system 800 and may interact with one or more nodes of computer system 800 through a wired or wireless connection, such as over network interface 840.

As shown in FIG. 8, memory 820 may include program instructions 825, configured to implement certain embodiments or the processes described herein, and data storage 835, comprising various data accessible by program instructions 825. In an embodiment, program instructions 825 may include software elements implementing the processes described above. For example, program instructions 825 may be implemented in various embodiments using any desired programming language, scripting language, or combination of programming languages and/or scripting languages (e.g., C, C++, C#, JAVA, JAVASCRIPT, PERL, etc.). Data storage 835 may include data that may be used in these embodiments. In other embodiments, other or different software elements and data may be included.

A person of ordinary skill in the art will appreciate that computer system 800 is merely illustrative and is not intended to limit the scope of the disclosure described herein. In particular, the computer system and devices may include any combination of hardware or software that can perform the indicated operations. In addition, the operations performed by the illustrated components may, in some embodiments, be performed by fewer components or distributed across additional components. Similarly, in other embodiments, the operations of some of the illustrated components may not be performed and/or other additional operations may be available. Accordingly, systems and methods described herein may be implemented or executed with other computer system configurations in which elements of different embodiments described herein can be combined, elements can be omitted, and steps can performed in a different order, sequentially, or concurrently.

The various techniques described herein may be implemented in hardware or a combination of hardware and software/firmware. The order in which each operation of a given method is performed may be changed, and various elements of the systems illustrated herein may be added, reordered, combined, omitted, modified, etc. It will be understood that various operations discussed herein may be executed simultaneously and/or sequentially. It will be further understood that each operation may be performed in any order and may be performed once or repetitiously.

The following definitions apply to certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. To the extent definitions for certain words and phrases are provided throughout this patent document, those of ordinary skill in the art should understand that in many, if not most, instances, such definitions apply to prior as well as future uses of such defined words and phrases.

Although the present disclosure has been described with an exemplary embodiment, various changes and modifications may be suggested to one skilled in the art. It is intended that the present disclosure encompass such changes and modifications as fall within the scope of the appended claims.

What is claimed is:

1. A security feature, comprising:
an intermingled luminescent material comprising a plurality of luminescent materials that, when individually excited in an absence of other luminescent materials, each produce emissions with a respective individual exponential decay characteristic,
wherein the intermingled luminescent material responds to excitation with emissions at a wavelength having a single, multi-exponential decay characteristic, the single multi-exponential decay characteristic different than all of the respective individual exponential decay characteristics for the plurality of luminescent materials.

2. The security feature according to claim 1, wherein the intermingled luminescent material is affixed to a brand product.

3. The security feature according to claim 1, wherein the individual exponential decay characteristics are a respective individual decay constant for emissions following excitation.

4. The security feature according to claim 3, wherein the plurality of luminescent materials are selected based on a ratio of the respective individual exponential decay characteristics, and wherein the ratio is greater than or equal to a predetermined ratio.

5. The security feature according to claim 1, wherein the plurality of luminescent materials are intermingled in the security feature to produce an overall decay of emissions from the intermingled luminescent material according to $$y = A_1 e^{-t/\tau_1} + A_2 e^{-t/\tau_2} + A_3 e^{-t/\tau_3} \ldots + A_n e^{-t/\tau_n}$$

where y is an intensity or amplitude of the emissions at time t, $A_n$ is an initial amplitude of emissions from an nth one of the plurality of luminescent materials following excitation and $\tau_n$ is a decay constant for emissions from the nth luminescent material following excitation.

6. The security feature according to claim 1, wherein the emissions of the plurality luminescent materials in response to the excitation are compared to one or more templates of multi-exponential curves to estimate a ratio of amounts of each of the plurality luminescent materials within the intermingled luminescent material.

7. The security feature according to claim 1, comprising a substrate in which the intermingled luminescent material is embedded.

8. A document including the security feature according to claim 1, wherein one or more emission responses of the intermingled luminescent material to excitation by light having a first wavelength and to excitation by light having a second wavelength is employed to identify the plurality of luminescent materials.

9. A method of authenticating a security feature, the method comprising:
    using an illumination source, exciting an intermingled luminescent material within the security feature, the intermingled luminescent material comprising a plurality of luminescent materials that, when individually excited in an absence of other luminescent materials, each produce emissions with a respective individual exponential decay characteristic, wherein the intermingled luminescent material responds to excitation with emissions at a wavelength having a single, multi-exponential decay characteristic, the single multi-exponential decay characteristic different than all of the respective individual exponential decay characteristics for the plurality of luminescent materials;
    using a sensor, measuring decay spectra from the security feature following excitation; and
    using a processing element,
        estimating a plurality of exponential decay characteristics from the measured decay spectra that combine to form the single multi-exponential decay characteristic, and
        identifying materials from a selected group of materials each corresponding to one of the plurality of estimated exponential decay characteristics forming the single multi-exponential decay characteristic.

10. The method according to claim 9, wherein the intermingled luminescent material is affixed to a brand product.

11. The method according to claim 9, wherein the individual exponential decay characteristics are a respective individual decay constant for emissions following excitation.

12. The method according to claim 11, wherein the plurality of luminescent materials are selected based on a ratio of the respective individual exponential decay characteristics, and wherein the ratio is greater than or equal to a predetermined ratio.

13. The method according to claim 9, wherein the plurality of luminescent materials are intermingled in the security feature to produce an overall decay of emissions from the intermingled luminescent material according to $$y = A_1 e^{-t/\tau_1} + A_2 e^{-t/\tau_2} + A_3 e^{-t/\tau_3} \ldots + A_n e^{-t/\tau_n}$$

where y is an intensity or amplitude of the emissions at time t, $A_n$ is an initial amplitude of emissions from an nth one of the plurality of luminescent materials following excitation and $\tau_n$ is a decay constant for emissions from the nth luminescent material following excitation.

14. The method according to claim 9, wherein the emissions of the plurality luminescent materials in response to the excitation are compared to one or more templates of multi-exponential curves to estimate a ratio of amounts of each of the plurality luminescent materials within the intermingled luminescent material.

15. The method according to claim 9, further comprising:
    using the illumination source, illuminating a substrate in which the intermingled luminescent material is embedded.

16. The method according to claim 15, further comprising:
    using the processing element, employing one or more emission responses of the intermingled luminescent material to excitation by light having a first wavelength and to excitation by light having a second wavelength to identify the plurality of luminescent materials.

17. An automated authentication device, comprising:
    an excitation source configured to illuminate the security feature for an article with light of at least one selected wavelength as the security feature is moved in front of the authentication device, the security feature including an intermingled luminescent material comprising a plurality of luminescent materials that, when individually excited in an absence of other luminescent materials, each produce emissions with a respective individual exponential decay characteristic, wherein the intermingled luminescent material is selected to respond to illumination with the light with emissions having a single, multi-exponential decay characteristic, the single multi-exponential decay characteristic different than all of the respective individual exponential decay characteristics for the plurality of luminescent materials;
    at least one sensor configured to receive emissions from the security feature for the article as the security feature is moved in front of the authentication device and measure decay spectra of emissions from the security feature; and
    a processing element configured to estimate a plurality of exponential decay characteristics from the measured decay spectra that combine to form the single multi-exponential decay characteristic.

18. The authentication device according to claim 17, wherein the article is a brand product.

19. The authentication device according to claim 17, wherein the plurality of luminescent materials are intermingled in the security feature to produce an overall decay of emissions from the intermingled luminescent material according to $$y = A_1 e^{-t/\tau_1} + A_2 e^{-t/\tau_2} + A_3 e^{-t/\tau_3} \ldots + A_n e^{-t/\tau_n}$$

where y is an intensity or amplitude of the emissions at time t, $A_n$ is an initial amplitude of emissions from an nth one of the plurality of luminescent materials following excitation and $\tau_n$ is a decay constant for emissions from the nth luminescent material following excitation.

20. The authentication device according to claim 17, wherein the security feature is moved in front of the authentication device using one of a document feeder and an article conveyor.

* * * * *